(12) United States Patent
Tayot

(10) Patent No.: US 8,853,361 B2
(45) Date of Patent: Oct. 7, 2014

(54) PREPARATION, FOR USE, IN PARTICULAR, FOR TISSUE AUGMENTATION AND HEALING

(75) Inventor: Jean-Louis Tayot, La Tour de Salvagny (FR)

(73) Assignee: Khorionyx, La Tour de Salvagny (FR)

( * ) Notice: Subject to any disclaimer, the term of this patent is extended or adjusted under 35 U.S.C. 154(b) by 919 days.

(21) Appl. No.: 12/375,705

(22) PCT Filed: Jan. 24, 2007

(86) PCT No.: PCT/FR2007/000137
§ 371 (c)(1),
(2), (4) Date: Jan. 30, 2009

(87) PCT Pub. No.: WO2008/015319
PCT Pub. Date: Feb. 7, 2008

(65) Prior Publication Data
US 2009/0312239 A1 Dec. 17, 2009

(30) Foreign Application Priority Data
Aug. 2, 2006 (WO) ................. PCT/FR2006/001880

(51) Int. Cl.
| | | |
|---|---|---|
| A61K 38/02 | (2006.01) | |
| A61K 38/17 | (2006.01) | |
| C07K 14/47 | (2006.01) | |
| C07K 17/02 | (2006.01) | |
| A61K 31/715 | (2006.01) | |
| A61P 19/00 | (2006.01) | |
| A61P 17/00 | (2006.01) | |
| A61L 15/32 | (2006.01) | |
| A61L 31/04 | (2006.01) | |
| A61L 24/10 | (2006.01) | |
| A61L 26/00 | (2006.01) | |
| A61L 27/46 | (2006.01) | |
| A61K 38/42 | (2006.01) | |
| A61L 27/20 | (2006.01) | |
| A61L 27/22 | (2006.01) | |
| A61K 38/39 | (2006.01) | |

(52) U.S. Cl.
CPC ............. A61K 38/42 (2013.01); A61L 15/32 (2013.01); A61L 31/047 (2013.01); A61L 24/108 (2013.01); A61L 26/0047 (2013.01); A61L 27/46 (2013.01); A61L 27/20 (2013.01); A61L 27/227 (2013.01); A61K 38/39 (2013.01)
USPC ....... 530/385; 424/70.13; 424/488; 514/16.7; 514/17.1; 514/18.6; 514/18.8; 514/54

(58) Field of Classification Search
None
See application file for complete search history.

(56) References Cited

U.S. PATENT DOCUMENTS

| | | | |
|---|---|---|---|
| 2,460,550 A | 2/1949 | Strumia et al. | |
| 2,597,432 A | 5/1952 | Beniams | |
| 3,640,741 A | 2/1972 | Etes | |
| 4,298,598 A | 11/1981 | Schwartz et al. | |
| 4,362,567 A | 12/1982 | Schwartz et al. | |
| 5,061,184 A | 10/1991 | Yamazaki et al. | |
| 5,173,301 A | 12/1992 | Itoh et al. | |
| 5,234,991 A | 8/1993 | Tayot et al. | |
| 5,356,883 A * | 10/1994 | Kuo et al. | 514/54 |
| 5,385,606 A | 1/1995 | Kowanko | |
| 5,410,016 A | 4/1995 | Hubbell et al. | |
| 5,573,934 A | 11/1996 | Hubbell et al. | |
| 5,874,500 A | 2/1999 | Rhee et al. | |
| 5,922,025 A | 7/1999 | Hubbard | |
| 5,986,043 A | 11/1999 | Hubbell et al. | |
| 6,019,993 A | 2/2000 | Bal | |
| 6,166,130 A | 12/2000 | Rhee et al. | |
| 6,440,427 B1 | 8/2002 | Wadström | |
| 6,624,245 B2 | 9/2003 | Wallace et al. | |
| 6,833,408 B2 * | 12/2004 | Sehl et al. | 525/54.1 |
| 6,943,154 B2 | 9/2005 | Miller et al. | |
| 6,949,625 B2 | 9/2005 | Tayot | |
| 2004/0248774 A1 * | 12/2004 | Tayot | 514/2 |
| 2005/0002893 A1 | 1/2005 | Goldmann | |
| 2005/0136122 A1 | 6/2005 | Sadozai et al. | |
| 2007/0031474 A1 | 2/2007 | Tayot | |

FOREIGN PATENT DOCUMENTS

| | | | |
|---|---|---|---|
| WO | PCT/US95/07947 | | 2/1996 |
| WO | WO 2004/082459 | * | 9/2004 |

* cited by examiner

*Primary Examiner* — Xiaozhen Xie
(74) *Attorney, Agent, or Firm* — B. Aaron Schulman, Esq.; Stites & Harbison, PLLC.

(57) ABSTRACT

The invention relates to a sterile preparation which can be implanted on or in organic tissues, comprising: a natural or modified globin material which is insoluble at physiological pH and/or a material obtainable from globin which has been modified to be soluble at physiological pH, the said materials being biocompatible and biodegradable in the organism; an agent selected from natural or synthetic polymeric adhesive agents, polymeric tissue enhancement or filling agents, more particularly an agent based on crosslinked hyaluronic acid or on polylactic acid, and a polymeric wound cicatrization agent, specifically oxidized cellulose; with the provisos that, if the preparation comprises the said material obtainable from globin modified so as to be at least partly soluble, the said polymeric adhesive agent, if present, is not hyaluronic acid or carboxymethylcellulose and the said polymeric enhancement or filling agent, if present, is an agent based on crosslinked hyaluronic acid, and that, if the preparation comprises oxidized cellulose, the latter is present in a proportion greater than that of the said globin material, which in that case is a natural or modified globin material which is insoluble at physiological pH; and the use of this preparation, more particularly for filling or cicatrization.

5 Claims, No Drawings

PREPARATION, FOR USE, IN PARTICULAR, FOR TISSUE AUGMENTATION AND HEALING

The object of the present invention is to provide new implantable or injectable preparations containing globin combined with non globin containing medical devices or products, in any proportion. The globin can, for example, constitute a quantitatively minor component of the final product. These preparations may, in particular, be in the form of powders, dressings, pastes, gels, injectable suspensions or solutions, or solid implantable materials, which are intended, in particular, to fill or repair tissular, cutaneous, conjunctive, vascular, visceral or osseous defects, and more generally to protect or fill wounds and contribute to the healing thereof. Various biomaterials consisting of natural or synthetic polymers, and which do not contain globin, are currently marketed and available for such medical and surgical uses. The main aim of the present invention is to improve their biocompatibility by favoring their cell colonization, proper tissular integration and their resorption.

Recently new materials and new medical applications based on globin that is insoluble at neutral pH under physiological conditions have been described and have been described in a family of patents based on patent FR 03 05700, published under number FR-A-2 854 801. These materials contain globin being insoluble at neutral pH as main active component.

Globin is the protein which constitutes hemoglobin, which itself contains 4 peptide chains (2 α chains and 2 β chains) each associated with one heme. The heme is formed by a tetrapyrole structure containing 1 positively charged iron atom. There are 4 hemes per molecule, and they are responsible for the red color of hemoglobin.

Processes for the preparation of globin have been known for a very long time and were developed for the purpose of application in foodstuffs or for the preparation of injectable pharmaceutical solutions.

Unlike hemoglobin which is very soluble at physiological pH, globin is remarkably insoluble under same conditions.

An injectable product combining a soluble preparation of acidic globin with insulin has been developed, patented and marketed: REINER (1939). REINER et al. (1939). After injection, it permits gradual release of insulin from this complex: RABINOWITCH et al. (1947); BERG et al. (1953). The globin of which this preparation is composed is not chemically modified. It is insoluble at physiological pH, present at low concentration, and is neither the active element nor the main element of this product.

It seemed interesting to us to manufacture composite biomaterials prepared by integrating soluble or insoluble globin into polymeric materials which were already are or may possibly be used as medical devices. Even under minor quantitative proportion, the presence of globin can improve the biological properties of these medical devices, and especially their biocompatibility, their cellular and tissular integration and their resorption.

The present invention proposes to provide new materials and preparations being implantable into the body, and comprising globin, either natural, or modified and insoluble at physiological pH, or chemically modified to be soluble under this condition. Such implants will not show the drawbacks or limitations of the existing, non globin containing materials.

The invention relates especially a sterile preparation, being implantable in or on organic tissues, comprising:
  a natural or modified globin material being insoluble at physiological pH and/or a material which is obtainable from globin modified to become soluble at physiological pH, which materials are biocompatible and biodegradable in the body,
  an agent selected among synthetic or natural adhesive polymeric agents, tissue filling or augmenting polymeric agents, especially an agent based on cross-linked hyaluronic acid, or on polylactic or other organic or mineral polymers, and a wound healing polymeric agent, namely oxidized cellulose,
  with the proviso that, if the preparation comprises said material which is obtainable from globin modified to become at least partially soluble, said adhesive polymeric agent, if present, is not hyaluronic acid nor carboxymethyl cellulose, and said filling or augmenting polymeric agent, if present, is an agent based on cross-linked hyaluronic acid, and that, if the preparation comprises oxidized cellulose, the latter is present at a proportion higher than said globin material, which, in this case, is a natural, or modified globin material being insoluble at physiological pH.

Insoluble modified globin means globin naturally insoluble at physiological pH, which was modified by addition of a hydrophobic molecule, for example, by esterification with a fatty alcohol.

Preferably, the polymeric adhesive agent is an agent based on at least one of the following materials: fibrinogen, albumin, an adhesive and biocompatible derivative of polyethylene glycol, or an adhesive and biocompatible acrylic or cyano-acrylic polymer.

Hyaluronic acid means, inter alia, the mucopolysaccharide extracted from bacteria or human tissues (such as placental cord) or animal tissues (such as rooster comb).

Cross-linked hyaluronic acid means, inter alia, the marketed injectable products for tissue augmentation, such as for example, Restylane®, Hylaform®, Juvederm®, Puragen Plus®. For example, cross-linking of the hyaluronic acid chains can be achieved by esterification activating agents such as carbodiimides as those disclosed in U.S. Pat. No. 6,943,154, which allow the carboxylic groups to react on the primary alcohol functions of the hyaluronic acid. Other agents which are well known for cross-linking polysaccharides are di-epoxy compounds, such as 1-4 butanedioldiglycidylether, which react, at alkaline pH, on the alcohol functions of polysaccharides. Epichlorohydrin is also an agent well known for cross-linking the polysaccharides at alkaline pH. Such examples are, inter alia, recited in U.S. Pat. No. 5,234,991.

Polylactic acid means any polymer which is mainly composed of monomers such as lactic acid which can be polymerized in presence of other monomers such as glycolic acid, in order to modulate their degradation time in the body, according to the state of the art.

In the preparation according to the invention, the natural or modified globin, being insoluble at physiological pH, and/or the soluble or insoluble material which is obtainable from globin which was modified, preferably chemically, to become soluble at physiological pH, for example this modified soluble globin itself, even if quantitatively minor with regard to the associated polymeric agent, form preferably the main active agent which improves the biocompatibility, the cell colonization or the tissular integration of the adhesive, or filling, or augmentation, or healing agent. Generally, this associated polymeric agent has only more limited, or even unexisting properties in those fields, and secures mainly an adhesion, filling, augmentation or protection function. If, as it is generally the case, said natural or synthetic adhesive polymeric agents, said tissue filling or augmenting polymeric agents, especially an agent based on cross-linked hyaluronic acid, or on polylactic or other organic or mineral polymers, or said wound healing polymeric agent, namely oxidized cellulose, show highly inflammatory properties, then the preparation according to this invention allows to provide, in the injected or implanted mass, less or not inflammatory areas, which leads to the above mentioned benefits.

Depending on the required goal, the proportion of the natural or modified globin, being insoluble at physiological pH and/or the material which is obtainable from globin which was modified, to become at least soluble at physiological pH, related to the sum, in weight, of this material and of the polymeric agent, can be higher than or equal to 50%. For example, one may prefer to reduce the content of expensive adhesive polymeric agent, e.g. fibrinogen or albumin, without impeding the adhesion features of the preparation.

However, one will mostly prefer this proportion to be lower or equal to 50%, for example less than 25% or even 10%, in order to obtain a preparation in which said material will improve the function of biocompatibility, cell colonization or tissular integration, without substantial dilution of the polymeric agent combined with it. It will, for example, be preferably the case for a preparation comprising a dominant amount of oxidized cellulose, or cross-linked hyaluronic acid or polylactic acid.

For example, in healing preparations according to the invention, which comprise a dominant proportion of oxidized cellulose, the latter secures its usual healing function, while the globin component or derivative implements the above mentioned functions, but can also, depending on its proportion, secure an own healing effect, as disclosed, for example, in patent application FR-A-2 854 801.

Similarly, in the filling preparations, this component can, in addition and depending on its proportion, implement an own filling function, as disclosed in the above mentioned French patent application.

Physiological pH means a pH between 6 and 8, preferably between 6.5 and 7.5 and more preferably the range of physiological pHs. Implantable means the capability of being implanted or injected into or on the body, in tissues or in contact thereof, including on the skin or on external wounds, with the exclusion of intravascular administration. It involves the possibility for them to be sterilized or directly prepared under sterile form.

Sterilization can be achieved, inter alia, through beta or gamma irradiation from 5 to 30 kGray. This irradiation can be conducted at room temperature or, for certain labile products, in the frozen state with the presence of dry ice. Autoclave sterilization, preferably at 120° C. is possible for insoluble globin.

In one embodiment, the material consists of, or is obtained from natural insoluble, non chemically modified globin. The concept of natural globin encompasses, of course, any equivalent globin which would have been obtained via synthesis or genetic recombination. Such preparations are disclosed in the above mentioned application FR 03 05700.

In another embodiment, the material is obtained from globin which was modified to become soluble at physiological pH, where this solubility may be total or partial. Such preparations were disclosed in French patent application FR 05 08392, filed on Aug. 5, 2005 and in PCT application PCT FR2006/001880, filed on Aug. 2, 2006, not yet published, and which are incorporated herein by reference.

In another embodiment, the material can be obtained from soluble modified globin and from globin, insoluble at physiological pH. Such preparations were disclosed in the above mentioned application FR 05 08392.

These implantable soluble or insoluble globin preparations are especially in the form of pastes or gels, solid materials like powder, granules, dressings, or films. They can be soluble or insoluble in a physiological liquid, or rendered insoluble after chemical cross linking of the soluble globin. They may be injectable. Injectable means the ability of being injected for local implantation, with the exclusion of any intra-venous or intra-arterial injection, which are both formally contraindicated.

Preferably the globin, in order to be rendered soluble at physiological pH, is chemically modified by alkaline treatment, preferably with NaOH, and/or by esterification of the carboxylic groups, and/or by acetylation or succinylation, to which its amine groups are responsive. Moreover said globin can be rendered partially soluble, through partial chemical reaction or an alkaline incubation, which is shorter or at a concentration lower than 1 N. For examples, treatments with NaOH concentrations from 0.1 to 1 N during 4 to 24 hours at room temperature, are possible. With higher concentration of NaOH or of another alkaline base, the duration of incubation and/or temperature can be reduced. Such treatments of globin were disclosed in patent FR 05 0892.

In one embodiment, said globin material is substantially soluble at physiological pH.

On the contrary, in another embodiment, said globin material is substantially insoluble at physiological pH, being prepared from either natural, or modified and insoluble globin, or obtained by cross-linking modified soluble globin.

The preparation can be under the form of a suspension, paste, solution or gel, being preferably sufficiently fluid in order to be injectable.

The preparation can comprise a powder of insoluble globin, or of globin modified to be soluble at physiological pH.

The globin preparations can be mixed with, or added to an adhesive synthetic or natural polymer, where the final mixture can form adhesive glue for organic tissues. Said adhesive polymeric agent forms, preferably, the liquid component of a glue preparation kit, and containing the not polymerized monomers or the not cross-linked polymers. It is not advised to mix the globin with the cross linking compound or the polymerization initiator as the latter would be consumed by the globin and rendered unavailable for the setting of the glue. Said adhesive polymeric agent can itself be under powder form, where the assembly may be formulated as a spray or an aerosol and form glue in the presence of a liquid medium, inter alia, a physiological liquid.

The preparations according to the invention can be in a one-piece form, preferably ready for use. But they can also be in the form of two or more components which are to be combined or mixed, for example, in the form of a kit, preferably in sterile form.

The value of this new family of products resides in particular in the fact that they are combined with a protein biomaterial which may be soluble or insoluble, as desired, and which are prepared from a defined, pure, homologous or autologous protein, which is completely biocompatible with the surrounding tissue into which they are injected. One can accordingly obtain, inside the implanted adhesive mass, a bioresorbable lattice to which the cells have access, and which dilutes and decreases the possible inflammatory potential of the implant, facilitates the tissular regeneration within the implant, its well adapted integration in the surrounding tissues, and its resorption.

Among the natural adhesive polymers, fibrinogen is already used for various medical and surgical applications. Thus it is possible, e.g. to combine in a new manner the plasmatic fibrinogen glues, said "fibrin glues", such as Tisseel®, Tissucol®, Quixil®, Hemaseal®, Beriplast® and others with adhesive or non adhesive, soluble or insoluble globin materials.

These fibrinogen based glues were described, mainly by the Immuno Company in the eighties; U.S. Pat. Nos. 4,298,598 and 4,362,567 or more recently by the Omrix Company: U.S. Pat. No. 6,019,993. The combination with globin gives a new opportunity which allows a rational use of the blood proteins, and leads to avoid them to be wasted, to lower the required doses, to improve their performance and to increase the number of their applications. These surgical glues according to the invention include a fibrinogen based material content, which is preferably lower than the usual content, and a soluble or insoluble material which can be obtained from soluble modified globin or from insoluble natural or modified globin, according to the invention.

Among the natural adhesive polymers, albumin was already used for various medical and surgical applications. It is then possible, for example, to combine, in a new manner, these albumin based glues with soluble or insoluble globin. As an example of albumin based glues, one can recite the Bioglue® glue resulting from the work of N. Kowanko (U.S. Pat. No. 5,385,606), marketed by the Cryolife Company. Other close products are disclosed in the following patent applications: H. Goldmann, J. Wegmann, PCT/EP02/11880; T. H. Barrows, T. W. Lewis, M. T. Truong, PCT/US95/07947.

Among the synthetic adhesive polymers, for example, derivatives of polyethylene glycol, or acrylic or cyano-acrylic polymers are already used in various medical and surgical applications. It is then possible, for example, to combine, in a new manner, the monomer component of these synthetic glues with soluble or insoluble globin, to improve their biocompatibility and tissular integration and to make their resorption easier. Among the marketed biological synthetic glues, as a non limiting example, one can recite glues based on reactive polyethylene glycol derivatives, such as Coseal® developed by the Cohesion Company, on the basis of U.S. Pat. Nos. 5,874,500; 6,166,130; 6,624,245; or Duraseal® developed by the Confluent Surgical Company; the products based on the U.S. Pat. No. 5,986,043; the FocalSeal® products developed by the Focal Company starting from various patents, including U.S. Pat. Nos. 5,410,016 et 5,573,934. Among the acrylic monomers based glues, one can recite, as non limiting examples, the Indermil® product developed by the Loctite Company and marketed by the Kendall Company; the Dermabond® product developed by the Closure Medical Company and manufactured by the Ethicon Company. Numerous other glues come from other synthetic or natural polymers, as for example the cellulose derivatives, and other patents or applications including: EP0488629, EP0310919, U.S. Pat. No. 3,640,741.

Human homologous globin is more preferred than heterologous animal globin, which allows to the best to avoid any immunological patient reaction, during or after implantation.

Globin is easy to purify from human red cells or blood. Human red cells are available in large quantities from outdated donations remaining in stock in blood transfusion centres and for which all the preliminary screening tests have been carried out when the blood was drawn. The preparations of implantable globin, or of other insoluble biomaterials based on the same globin therefore represent a new way for satisfying biomedical applications which are increasingly developing, while at the same time making good use of unused blood or outdated blood donations and avoiding or reducing their wasting. In contrast to other proteins, including collagens, globin has the original feature of preserving its properties despite prolonged alkaline treatment and/or despite sterilization by irradiation. This enables it to be used entirely safely, thanks to the guarantee of a powerful inactivation of the infectious or transmissible agents potentially present in any product of biological origin.

The implementation of the invention is also possible starting from a blood sample of a patient to be treated e.g. approximately from 20 to 200 ml, and its conversion into autologous globin using the same methods as for large volumes, then its conversion into implantable biomaterial for the invention.

The implementation of the invention may first of all require the collection and purification of the red cells from these blood samples, or blood liquids, by simple operations which are already known, for example in accordance with the following process.

The red cells are recovered by low-speed centrifugation. The plasma supernatant is separated and replaced by a physiological saline liquid, containing 9 g/l of NaCl. After several washes (3 to 5), the suspension of red cells is thus freed from the plasma proteins. 1 or 2 volumes of distilled water are added to the purified red cells pellet in order to get an osmotic shock which brings about the lysis of the red cells membranes corpuscles and frees the hemoglobin in a concentrated and purified solution. A step of high-speed centrifugation (10 to 20,000 rpm) enables the membrane debris and cell debris in the pellet to be eliminated. A final filtration step of the supernatant through a membrane having a porosity of 0.2 micron permits the preparation of a purified and sterile hemoglobin solution free from particles and derivatives of tissue, cellular or membrane origin. Thus, for the hemolysis step of the red cells, the latter can be purified, in order to start from a purified hemoglobin solution already freed of plasmatic components. But this step can be omitted, inter alia due to the specific insoluble character of globin in an aqueous solution of neutral pH, which differentiates it from the other plasma proteins and allows its separation.

The heme-globin cleavage at acidic pH was described in the presence of alcohol by SCHULZ as early as 1898. ANSON and MIRSKY in 1930, then ROSSI-FANELLI et al. in 1958 use acetone in the presence of acid at 0° C. TEALE (1959) prefers the use of methyl ethyl ketone instead of acetone. AUTIO et al. (1984) separate the globin at acidic pH owing to the absorption and precipitation of the heme with soluble carboxymethylcellulose. The globin thus prepared is soluble at acidic or alkaline pH but becomes insoluble as soon as the pH of the aqueous solution is neutralized to pH 6 to 8. Owing to this specific property, it becomes possible to obtain a selective precipitation of the globin in aqueous solution at neutral pH, preferably at a low salt concentration, e.g. close to NaCl 5 g/l, where the other plasmatic proteins remain soluble in these conditions, do not co-precipitate with globin and are separated in the supernatant. This method is useful where one wishes to avoid to first separating the red cells from the plasma, which allows freezing the blood as soon as the sample is drawn.

In this case, the blood is hemolyzed, preferably through freezing followed by thawing, where, thereafter, the heme is dissociated and separated by a suitable agent, for example acetone, the globin and other proteins containing fraction is put under liquid form and neutralized, whereby the globin is precipitated, and at least partially separated from the other protein components of blood.

As an example, human blood is sampled from a patient and recovered in the presence of an anticoagulant agent, such as sodium citrate or heparin, while stirring. The sample is immediately frozen. After thawing, the blood is added with distilled water to complete hemolysis, and then preferably clarified by filtration or centrifugation. The clarified blood solution is poured into about 10 volumes of acidified acetone under stirring, at room temperature. The dissolved heme containing acetone is eliminated by filtration through a porous mesh. The precipitate of plasmatic proteins and unpigmented globin is washed on the mesh with anhydrous acetone and recovered by pressing. Thereafter the precipitate is redissolved in a NaCl containing aqueous solution. A filtration step on a porous membrane allows to eliminate the insoluble denatured plasmatic impurities. Then the filtrate is neutralized and the globin heavily precipitates, leaving the soluble plasmatic proteins in the supernatant. The neutral purified globin precipitate is washed on a filtration mesh with a physiological solution. The simplicity of the method allows making it automatic, which permits a quick and economic preparation of homologous or heterologous globin.

In a surprising manner one can thus obtain concentrated and particularly fluid whitish globin preparations.

The invention also relates to the use of a preparation according to the invention for producing a preparation which is implantable or injectable in the body.

The use according to the invention permits, especially, to improve the biocompatibility, the cell colonization or the tissular integration, or the resorption of the adhesive, filling, augmentation or healing agent present in the preparation.

Thus this use can, especially, be directed to the production of an adhesive preparation for:
- the healing, protection or filling of external skin wounds or internal surgical wounds,
- the filling of wrinkles and skin folds,
- the filling of connective tissues or sphincters for applications in urology: vesico-ureteral reflux in children, stress incontinence in women; in ENT: correction of vocal cords volume,
- adhesive and haemostatic plug for tissue wounds or percutaneous arterial wounds,
- means for fixing prostheses or biomaterials to receiver tissues, especially for fixing devices for parietal and visceral reinforcement
- or films, gels and membranes for preventing post-operative adhesion, used alone or in combination with other medical devices.

Finally, the invention relates to a method of cosmetic or therapeutic treatment, wherein one delivers, to a patient in need thereof, a cosmetically or therapeutically effective amount of a preparation according to the invention.

This method relates especially to the above mentioned uses.

The following examples illustrate, in a non limiting manner, the embodiment of the invention for improving the biocompatibility of the glues and implants, presently used in medicine and surgery.

EXAMPLES OF PRODUCTION METHODS OF PRODUCTS ACCORDING TO THE INVENTION

Example 1

Preparation of Human Globin Insoluble at Physiological pH 30 ml of human blood are sampled from a patient by venous puncture and recovered under stirring with 3 ml of sodium citrate. The sample is immediately frozen. After thawing, the blood is added with an equal volume of distilled sterile water for completion of the hemolysis, and then centrifuged during 30 mn at 10 000 rpm, and/or clarified on prefilters and submitted to sterile filtration through a 0.2 to 0.45 micron porosity membrane. After filter rinsing, a volume of 74 ml is obtained, which contains 52 mg/ml hemoglobin and is stored at 4° C. This solution is gently poured, under stirring, into 750 ml acetone, which contains 7.5 ml HCl 12N. The suspension is strongly stirred and allowed to rest during 10 to 60 mn at room temperature under a chemical hood or in a tight reactor. The dissolved heme containing acetone is separated by filtering on a porous mesh. The decoloured globin precipitate is washed on the mesh with anhydrous acetone and recovered after pressing. Vacuum drying permits to prepare globin powder of white colour, which globin can be easily stored or transported, if needed. The globin precipitate (21.8 g) or the corresponding powder is then redissolved in 300 ml distilled sterile water, and the solution is added with 5 g/l NaCl. The acidic pH (=2.5) is adjusted at a 5 to 5.5 value by addition of NaOH 1 N. The globin remains soluble under these conditions and a filtration on a porous membrane allows eliminating the insoluble denatured plasmatic contaminants. The filtrate is then adjusted at pH 7.0 and the globin precipitates heavily, where the soluble plasmatic proteins remain in the supernatant. The neutral precipitate of purified globin is washed on a filtration mesh with a NaCl 5 g/l solution. A supplementary purification can be achieved through acidic dissolving, filtration through a porous sterilizing membrane of 0.2 to 0.45 micron and reprecipitation at neutral pH. On the other hand an alkaline treatment with a final 0.2 N sodium hydroxide concentration during 1 hour at +20° C., followed by a precipitation at neutral pH by addition of HCl 1 N, allows securing complementary inactivation of infectious or transmissible agents possibly present in the patient's blood. Finally the insoluble globin paste is suspended in a physiological 9 g/l NaCl solution, possibly buffered at pH 7. In a variation, the globin precipitate can be washed with distilled water, and then submitted to a lyophilisation step, in order to prepare a neutral insoluble globin powder. Adding sodium hyaluronate or plasticising agents, such as glycerine and/or polyethyleneglycol allows to prepare more or less complex globin powders, for later mixing with adhesive biomaterials. Finally the paste or powder of insoluble globin may be sterilized by beta or gamma irradiation at a dose of 5 to 30 kGray.

Example 2

Preparation of Human Globin, Chemically Modified and Soluble at Physiological pH The method of Example 1 is carried out, starting from a controlled and outdated 400 ml red cells concentrate pouch which was obtained from a blood transfusion centre. The volumes of the reactants are proportionally adapted to the volume to be treated. At the end of the purification, the globin precipitate is redissolved at an acidic pH between 2 and 3. The globin is precipitated within 10 volumes of acetone and then washed with anhydrous acetone and dried under vacuum or under air flow, with constant stirring, so as to prepare a finely comminuted, salt free, acidic powder. One weighs 8 g finely comminuted human globin powder in a 250 ml flask, to which one adds 200 ml anhydrous ethanol containing 2 ml HCl 12 N, resulting in a 0.12 N final acid concentration. Under these conditions the powder remains perfectly insoluble, swells slightly and is well dispersed. After the flask is hermetically corked, one week incubation is conducted at room temperature, with mild agitation several times a day.

The globin precipitate is separated from the acidic ethanol, through a 1 micron porosity Nylon mesh. The precipitate is washed three times with 200 ml pure acetone and air dried, to obtain 7.4 g of a fine and well comminuted powder. Finally the soluble globin powder can be sterilized by beta or gamma irradiation at 5 to 30 kGray.

This spontaneously poorly wettable powder can be quickly dissolved in 200 ml distilled water, in a beaker. It results in a straw yellow transparent solution having a 2.8 pH value. Neutralizing the pH of this solution by dropwise addition of 0.5N NaOH, under hand stirring and continuous pH control, allows to verify the soluble character of the globin at a neutral pH between 6 and 8, and then its massive precipitation at an alkaline pH close to 9.5 to 10.

It is possible to observe an early precipitation towards pH 6. This is related to the partial presence of unmodified globin, which was protected from the esterifying reaction inside a large powder aggregate. One should notice that the so prepared globin esters are gradually hydrolysed in vivo, and lead to spontaneous regeneration of the initial insoluble globin, which itself will be degraded. This accordingly corresponds to a chemical reaction which is reversible with time, or in vivo. One should also notice that the so prepared globin esters have a very marked positive electric charge. Their alcaline isoelectric pH, close to 10, results from the more or less complete disappearance of the carboxylic groups. This feature brings them an adhesive character with regard to negatively charged tissues. These globin esters have a large amount of amine groups which can readily be cross-linked by the usual reagents of the biological glues including aldehyde functions, such as glutaraldehyde or oxidized polysaccharides. Furthermore, they can readily form stable lattices owing to strong electrostatic bonds, in the presence of any negatively charged polymer or biopolymer. Among synthetic polymers, one can list, for example, the polyacrylic polymers or the anionic derivatives of the polyethylene glycols. Among the natural polymers, one can list fibrinogen, fibrin, albumin, hyaluronates, heparin, the bioresorbable cellulose derivatives, such as oxidized cellulose, or any other sulphated or many carboxylic groups bearing polysaccharides.

Example 3

Preparation of Human Globin, Chemically Modified and Insoluble at Physiological pH If the ethanol used in example 2 is replaced by a fatty alcohol, which has a chain of at least 4 carbon atoms, such as butanol, hexanol, octanol, or which even has a longer chain, the obtained esterified globin derivative is no more soluble at neutral pH, but becomes insoluble in water or in an aqueous physiological solution. In order to facilitate the esterification reaction of the carboxylic groups of the globin by a long carbon chain alcohol, it is preferred to use usual activation means, such as carbodiimides or other known alcohol or carboxylic groups activating agents.

Example 4

Preparation of Human Globin, Chemically Modified and Insoluble at Physiological pH 5 g of esterified soluble globin powder, which were prepared according to example 2, are suspended in 200 ml of an aqueous 50% ethanol containing solution, which also contains glutaraldehyde at a 0.25% concentration. After one hour incubation at room temperature, the cross-linked globin solution is added with 2 g sodium borohydride, inside a chemical hood for evacuating the excess of generated native hydrogen. This fast reaction achieves the reduction of the aldehyde groups in excess and transforms them into alcohol groups. The so treated globin suspension looses the yellow colour which was caused by the glutaraldehyde. Thereafter it is washed in ethanol and then in acetone and vacuum dried, for preparing a whitish insoluble cross-linked globin powder.

Example 5

Combination of a Sterile Insoluble Globin Powder with Commercial Biological Glues The powder of insoluble globin, prepared according to one of examples 1, 3 and 4, can be used as an additive to the liquid component of the medical or surgical glues. This powder does not dilute the active principle (monomers or soluble polymers) of the commercially used biological glue. The two components of these biological glues can be mixed in the same way. The globin does not impede the final polymerization or cross-linking reaction of the assembly to which the globin is part, once the polymerization catalyst or the cross-linking agent is added. This mixture can be carried out with a suitable sterile mixer, just before the glue is used, or can be integrated in the manufacturing method of the liquid component of the biological glue. The globin lattice inserted inside the glue forms an entrance way for the cells which will contribute to the progressive tissular reconstruction of this glue volume, and to its harmonious integration with the surrounding tissues. This addition of globin is easily performed with the soluble component of the usual implantable glues; for example, the fibrinogen based glues such as TISSEEL®, BERIPLAST®; albumin based glues such as BIOGLUE®; polyethylene glycol derivative based glues such as COSEAL®, DURASEAL®; or acrylic derivative based glues such as INDERMIL®, or DERMABOND®.

Example 6

Combination of a Sterile Insoluble Globin Paste with Commercial Biological Glues The above Example 5 is reproduced while replacing the globin powder by an aqueous globin paste prepared according to one of examples 1, 3 and 4. The diluting effect of the adhesive agent, bringing by water contained in the globin paste is immaterial, and greatly compensated by the added globin, which participates to the new adhesive mixture, while thickening it and increasing its viscosity and texture. Moreover this water does not come to mix, if the adhesive component is in an organic solution immiscible with water.

Example 7

Combination of a Soluble Sterile Globin Powder with Commercial Biological Glues

The above examples 5 and 6 are reproduced by using the soluble globin powder prepared according to example 2. In this case the globin does not induce any dilution. After the new adhesive mixture is implemented in vivo, the globin powder gradually absorbs the water of the surrounding tissues, which will form the new entrance way of the cells for the colonization, the tissular integration and the gradual resorption of the implant.

Example 8

Combination of an Insoluble Globin paste with Oxidized Cellulose Fibres

A paste of insoluble globin is prepared, preferably according to one of examples 1, 3 or 4. This insoluble globin paste in suspension, for example in distilled water, is mixed with a paste of oxidized cellulose fibres at a ratio of 20 and 80%, respectively. The mixture is lyophilized and sterilized by gamma irradiation at a dose of 25 to 30 kGray. It results in a composite sponge of oxidized cellulose and insoluble globin for treating internal or external wounds. The ratio of globin and oxidized cellulose can be changed in order to optimize the healing capacity and the resorption rate of the biomaterial, said globin ratio being less than 50%.

Example 9

Association of an Insoluble Globin Paste with a Cross-Linked Hyaluronate Gel An insoluble globin paste is prepared, preferably according to one of examples 1, 3 or 4. This insoluble globin paste, preferably at a 10% concentration, and suspended in a physiological solution, for example 9 g/l NaCl, is packaged in 1 ml plastic or glass syringe (Schott or Becton Dickinson) and sterilized by gamma irradiation at a dose of 25 to 30 kGray. The sterile insoluble globin paste is then mixed with a sterile gel of cross-linked hyaluronate, at any possible ratio, e.g. through a sterile coupling connector, for example a polypropylene one of the luer lock type, provided by Promepla, Monaco, (ref FTLLC-6). The coupler can possibly have a restriction diameter between 0.2 and 2 mm. The cross-linked hyaluronate can be any one of the marketed products: Restylane® or Hylaform® or Juvederm® or Puragen Plus® or any equivalent product. The sterile mixture of the two polymers is directly obtained in a syringe, preferably of 1 ml, at any possible ratio, and can be injected for the required tissue augmentation. Such composite product allows cells to colonize the implant, owing to the presence of insoluble globin inside the cross-linked hyaluronate gel, even in a minor amount.

It is possible to combine other filling or augmentation products or polymeric preparations with natural or modified insoluble globin, or globin which was modified to be at least partially soluble, such as polylactic acids, e.g. according to the following example.

Example 10

Combination of an Insoluble Globin Paste with a Suspension of Polylactic Acid Microparticles A paste of insoluble globin is prepared, preferably according to one of examples 1, 3 or 4. This paste of insoluble globin, preferably at a 10% concentration, and suspended in a physiological solution, for example at 9 g/l NaCl, is packaged in 1 ml plastic or glass syringes (Schott or Becton Dickinson) and sterilized by gamma irradiation at a dose of 25 to 30 kGray. The obtained sterile insoluble globin paste is then mixed with a sterile suspension of polylactic acid microparticles at any possible ratio, e.g. through a sterile coupling connector, for example a polypropylene one of the luer lock type, provided by Promepla, Monaco, (ref FTLLC-6). The coupler can possibly have a restriction diameter between 0.2 and 2 mm. The suspension of polylactic acid microparticles can be obtained, for example, from the Sculptra® product marketed by the Dermik Company or any other injectable polylactic acid paste provided for tissue filling. The sterile mixture of the two biopolymers is directly obtained in a syringe, preferably of 1 ml, at any possible ratio, and can be injected for the required tissue augmentation. Such composite product allows better, more stable and less inflammatory cell colonization of the implant, owing to the presence of insoluble globin inside of the implanted product, even in a minor amount.

Example 11

Combination of an Insoluble Globin Paste with Mineral Particles

A paste of insoluble globin is prepared, preferably according to one of examples 1, 3 or 4. This paste is mixed with a suspension of mineral particles consisting of calcium phosphate or hydroxylapatite, for example at 20% and 80% respective ratio. This assembly is dried under sterile air flow, or freeze-dried and sterilized by gamma irradiation at a 25 to 30 kGray dose. One obtains a composite powder of coated mineral particles (if dried) or mixed particles (if freeze-dried) with insoluble globin, for treating bone fractures or defects. The ratio of globin and mineral particles can be modified for optimizing the bone healing capacity and the resorption rate of the biomaterial, where the globin ratio is preferably less than 50%. If orthopaedic prostheses are coated with mineral particles for improving their bio-integration, the addition of globin to this granular coating is specially indicated.

The preparations which combine a material of globin, either natural, or modified and insoluble at physiological pH, and/or a material which can be obtained from globin which is chemically modified to be at least partially soluble at physiological pH, with mineral particles, especially consisting of calcium phosphate or hydroxylapatite, e.g. according to example 11, and which may have a respective ratio, preferably from 10/90 to 90/10, can be used not only for filling soft tissues, for example cutaneous tissue, especially wrinkles, preferably by combining said material with hydroxyl-apatite, but also for bone filling or repair, including in the stomatology field and in dental surgery, for example for treating periodontitis.

Example 12

Medical Applications of the Globin Containing Biomaterials and Biological Glues The biomaterials and biological glues which combine globin, even in a minor ratio, according to the invention can be used in the following, not limited, applications.

- the healing, protection or filling of external skin wounds or internal surgical wounds,
- the filling of wrinkles and skin folds,
- the filling of connective tissues or sphincters for applications in urology: vesico-ureteral reflux in children, stress incontinence in women; in ENT: correction of vocal cords volume,
- adhesive and hemostatic plug for tissue wounds or percutaneous arterial wounds,
- means for fixing prostheses or biomaterials to receiver tissues, especially for fixing devices for parietal and visceral reinforcement
- films, gels and membranes for preventing post-operative adhesion, used alone or in combination with other medical devices.

The filling and healing of bone wounds and the coating of orthopaedic prostheses.

The present invention thus also relates to the use of the combination, according to the invention, of a natural globin or modified globin material being insoluble at physiological pH and/or a material which is obtainable from globin modified to become at least partially soluble at physiological pH, which materials are biocompatible and biodegradable in the organism, and of an agent selected from synthetic or natural adhesive polymeric agents, tissue filling or augmenting polymeric agents, especially an agent based on cross-linked hyaluronic acid, or on polylactic acid or other organic or mineral polymers, especially hydroxyapatite and a wound healing polymeric agent, namely oxidized cellulose, with the provision that, if the preparation comprises said material which is obtainable from globin modified to become at least partially soluble, said adhesive polymeric agent, if present, is not hyaluronic acid nor carboxymethyl cellulose, and said filling or augmenting polymeric agent, if present, is an agent based on cross-linked hyaluronic acid, and that, if the preparation comprises oxidized cellulose, the latter is present at a ratio higher than said globin material, which, in this case, is a natural, or modified globin material being insoluble at physiological pH, for the production of an injectable or implantable preparation, according to the invention, especially for one or several above mentioned applications.

In general, irrespective of the preparation according to the invention, the methods have a therapeutic aim. Methods for filling wrinkles may, depending on the person concerned, have a purely cosmetic aim. In any case, the method according to the invention comprises the step of implanting locally, in or on the tissue of the patient or the person in need thereof, a therapeutically or cosmetically effective amount of a preparation according to the invention, in particular for the above-mentioned applications.

BIBLIOGRAPHY

ANSON M. L.-MIRSKY A. E. (1930)
Protein Coagulation and its reversal. The preparation of insoluble globin, soluble globin and heme.
J. Gen. Physiol. 13, 469-476
AUTIO K-KIESVAARA M.-MALKKI Y.-KANKU S. (1984)
Chemical and functional properties of blood globin prepared by a new method
Journal of Food Science 49, 859-862
BERG J. W.-ORTMEYER D. W.-OTT D. L.-JACKSON R. L. (1953)
Comparison of Globin Insulin and NPH Insulin
Diabetes, 2, 5, p. 365-369
RABINOWITCH I. M.-FOWLER A. F.-BENSLEY E. H.-GORDON A. L.-MOUNTFORD M. (1947)
Globin Insulin
The Canadian Medical Association J., 56, 6, p. 595-605
REINER L. (1939)
Insulin preparation
U.S. Pat. No. 2,161,198
REINER L.-SEARLE D. S.-LANG E. H. (1939)
Insulin preparations with prolonged activity
I. Globin Insulin
Proc. Soc. Exp. Biol. Med. 40, p. 71
ROSSI-FANELLI A.-ANTONINI E.-CAPUTO A. (1958)
Studies on the structure of haemoglobin
I-Physicochemical properties of human globin
Biochem. Biophys. Acta 30, 608-615
SCHULZ F. N. (1898)
Der Eiweisskörper des hämoglobins
Ztsch. F. physiol. chem. 24, 449-460
TEALE F. W. J. (1959)
Cleavage of the haem-protein link by acid methyl-ethyl keton
Biochem. Biophys. Acta 35, 543

The invention claimed is:

1. A sterile paste or suspension preparation being injectable in or on organic tissues, comprising, in a liquid vehicle:
a globin material which comprises globin and is biocompatible and biodegradable in the body, and
a tissue filling or augmenting polymeric agent;
wherein said globin in said globin material consists of natural globin which is insoluble at physiological pH; and
wherein said tissue filling or augmenting polymeric agent is a cross-linked hyaluronic acid and is present at a ratio equal to or higher than said globin material.

2. A preparation according to claim 1, wherein said natural globin is human globin.

3. A preparation according to claim 1, wherein the ratio of said globin material compared to the total globin material and cross-linked hyaluronic acid weight is lower than or equal to 25%.

4. A preparation according to claim 1, wherein the ratio of said globin material compared to the total globin material and cross-linked hyaluronic acid weight is lower than or equal to 10%.

5. A method for filling or healing a cutaneous, conjunctive, or bone defect, comprising administering to the defect site an effective amount of a preparation according to claim 1.

* * * * *